United States Patent
Tani et al.

(10) Patent No.: US 9,006,477 B2
(45) Date of Patent: Apr. 14, 2015

(54) METHOD FOR PRODUCING NITROBENZENE COMPOUND

(75) Inventors: Shinki Tani, Shizuoka (JP); Nami Yadomatsu, Shizuoka (JP); Akiko Ikumi, Shizuoka (JP); Yuuki Hirano, Shizuoka (JP); Takuya Ido, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 14/131,106

(22) PCT Filed: Jul. 4, 2012

(86) PCT No.: PCT/JP2012/004320
§ 371 (c)(1),
(2), (4) Date: Jan. 6, 2014

(87) PCT Pub. No.: WO2013/005425
PCT Pub. Date: Jan. 10, 2013

(65) Prior Publication Data
US 2014/0163256 A1    Jun. 12, 2014

(30) Foreign Application Priority Data

Jul. 7, 2011   (JP) ................................ 2011-151276
Mar. 21, 2012  (JP) ................................ 2012-063751

(51) Int. Cl.
C07C 205/06   (2006.01)
C07C 201/06   (2006.01)

(52) U.S. Cl.
CPC .................................... *C07C 201/06* (2013.01)

(58) Field of Classification Search
CPC ......................... C07C 201/06; C07C 2015/06
USPC .................................... 560/20; 562/438, 441
See application file for complete search history.

(56) References Cited

FOREIGN PATENT DOCUMENTS

| JP | 2001-139526 A | 5/2001 |
| JP | 2003-261516 A | 9/2003 |

OTHER PUBLICATIONS

Machine translation of JP 2003-261516.*
Mashine translation of JP 2001-139526.*
Zhao et al, J. Org. Chem Soc. 2010, 75, 10, 3311-3316.*
Sakaue et al.; "Oxidation of Aromatic Amines with Hydrogen Peroxide Catalyzed by Cetylpyridinium Heteropolyoxometalates", J. Org. Chem., 1993, vol. 58, p. 3633-3638.
International Search Report in PCT/JP2012/004320, Aug. 7, 2012.

* cited by examiner

*Primary Examiner* — Yong Chu
*Assistant Examiner* — Ana Z Muresan
(74) *Attorney, Agent, or Firm* — Bacon & Thomas, PLLC

(57) ABSTRACT

A method for producing a nitrobenzene compound represented by general formula (2), wherein $R^1$ and $R^5$ are the same or different, and each is a halogen atom or another functional group, and $R^2$, $R^3$, and $R^4$ are the same or different, and each is a hydrogen atom or another functional group, comprises oxidizing an aniline compound represented by general formula (1), wherein $R^1$, $R^2$, $R^3$, $R^4$, and $R^5$ are the same as described above, with hydrogen peroxide in the presence of a tungsten compound under an acidic condition, followed by oxidation with hydrogen peroxide under a neutral to alkaline condition.

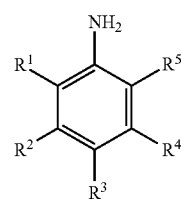

(1)

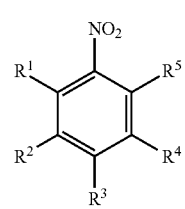

(2)

21 Claims, No Drawings

METHOD FOR PRODUCING NITROBENZENE COMPOUND

TECHNICAL FIELD

The present invention relates to a method for producing a nitrobenzene compound, particularly a 2,6-disubstituted nitrobenzene compound. This 2,6-disubstituted nitrobenzene compound is useful, for example, as intermediates for the synthesis of various organic compounds (for example, physiologically active organic compounds such as medicines and agrochemicals).

BACKGROUND ART

Nitrobenzene compounds, particularly 2,6-disubstituted nitrobenzene compounds, are widely known as intermediates for the synthesis of various organic compounds, as described above. Particularly, 2,6-dichloronitrobenzene is reported as an intermediate for synthesis for producing a compound described as an EP4 receptor antagonist (see Example 55, Patent Literature 1), or as an intermediate for synthesis for producing a compound described as a brakykinin $B_1$ receptor antagonist (see Example 8 and Example 104, Patent Literature 2). In addition, it is also known as an intermediate for synthesis for producing a hair dyeing composition (see Production Example 6 and Example 10, Patent Literature 3).

Similarly, 2-chloro-6-alkoxycarbonylnitrobenzene is also known as a beneficial intermediate, and is known as an intermediate for synthesis for producing a compound described as an inhibitor of protein tyrosine phosphatase (see Example 76, Patent Literature 4), or as an intermediate for synthesis for producing a compound having high herbicidal activity {see (2)-(5), Synthesis of Compound 2, Patent Literature 5}.

Further, it is also known that 2-chloro-6-methoxymethylnitrobenzene, which is a useful intermediate for an agrochemical, can be produced from 2-chloro-6-alkoxycarbonylnitrobenzene by subjecting it to methylolation by reduction, followed by methoxymethylation (see Patent Literature 6).

With regard to nitrobenzene compounds from which useful compounds can be produced as described above, it has been conventionally known that in the oxidation of an aniline compound to a nitrobenzene compound with industrially inexpensive hydrogen peroxide, the reaction proceeds easily in the oxidation of the aniline compound to the nitrobenzene compound when the ortho position with respect to the amino group of the aniline compound is not substituted (Patent Literature 7). However, when an attempt is made to conduct the oxidation of a 2,6-disubstituted aniline compound under the same conditions, the target 2,6-disubstituted nitrobenzene compound cannot be obtained with good yield (see Comparative Examples 1 and 2). Therefore, conventionally, it has been necessary to use high concentration hydrogen peroxide, which requires much caution in work, and further use a high risk organic peroxy acid such as peracetic acid or trifluoroperacetic acid in order to obtain a 2,6-disubstituted nitrobenzene compound from a 2,6-disubstituted aniline compound (Non Patent Literature 1 and Non Patent Literature 2), and there has been no synthesis method for producing a 2,6-disubstituted nitrobenzene compound under mild conditions.

Patent Literature

Patent Literature 1: Published Japanese Translation of PCT Application, Publication No. 2005-533756 (JP-A-2005-533756)
Patent Literature 2: Published Japanese Translation of PCT Application, Publication No. 2008-537953 (JP-A-2008-537953)
Patent Literature 3: Japanese Patent Application Laid-Open No. shou-62-246967 (JP-A-1987-246967)
Patent Literature 4: International Publication No. WO2005/081960
Patent Literature 5: U.S. Pat. No. 5,084,086
Patent Literature 6: International Publication No. WO2000/006553
Patent Literature 7: Japanese Patent No. 4284999

Non Patent Literature

Non Patent Literature 1: Jikken Kagaku Koza (Experimental Chemistry Course), 4th ed., Vol. 20, Yukigosei (Organic Synthesis) II, p. 402 (1992, Maruzen Company, Limited)
Non Patent Literature 2: Organic Syntheses, Col. Vol. V, p. 367

SUMMARY OF INVENTION

It is an object of the present invention to provide a method for producing a nitrobenzene compound, particularly a 2,6-disubstituted nitrobenzene compound, that can solve one or more drawbacks in the prior art described above.

Specifically, it is an object of the present invention to provide a method that can produce a high purity nitrobenzene compound with high yield on an industrial scale production by a simple operation under mild conditions, while suppressing generation of waste as a by-product, using hydrogen peroxide which is inexpensive, becomes harmless water after a reaction, and attracts attention as a clean and excellent oxidant, but without using high risk, high concentration hydrogen peroxide, and further even without using a high risk organic peroxy acid such as peracetic acid or trifluoroperacetic acid.

In view of the circumstances as described above, the present inventor has repeated studies on methods for producing nitrobenzene compounds diligently, particularly 2,6-disubstituted nitrobenzene compounds, and, as a result, unexpectedly found that the above problem can be solved by using an aniline compound and a tungsten compound, and reacting them with hydrogen peroxide under an acidic condition followed by reaction with hydrogen peroxide under a neutral to alkaline condition, even without using high concentration hydrogen peroxide. Based on this finding, the present inventor has completed the present invention.

Specifically, the present invention solves the above problem by providing inventions according to the following items [1] to [29].

[1] A method for producing a nitrobenzene compound represented by general formula (2):

[Formula 2]

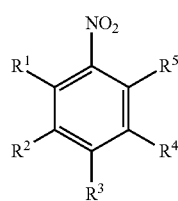

(2)

(wherein $R^1$ and $R^5$ are the same or different, and each is a halogen atom, a C1 to C4 alkoxycarbonyl group, a C1 to C4 alkyl group, a C1 to C4 alkoxy group, or a C1 to C4 alkoxy C1 to C4 alkyl group, and $R^2$, $R^3$, and $R^4$ are the same or different, and each is a hydrogen atom, a halogen atom, a C1 to C4 alkyl group, a C1 to C4 alkoxy group, or a C1 to C4 haloalkyl group.)

comprising oxidizing an aniline compound represented by general formula (1):

[Formula 1]

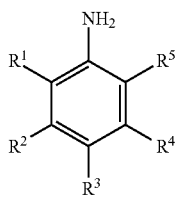

(1)

(wherein $R^1$, $R^2$, $R^3$, $R^4$, and $R^5$ are the same as described above.)

with hydrogen peroxide in the presence of a tungsten compound under an acidic condition, followed by oxidation with hydrogen peroxide under a neutral to alkaline condition.

[2] The method for producing a nitrobenzene compound according to [1], wherein oxidation of the aniline compound represented by general formula (1) to the nitrobenzene compound represented by general formula (2) with hydrogen peroxide is conducted by changing a pH condition in the oxidation reaction from an acidic condition to a neutral to alkaline condition.

[3] The method for producing a nitrobenzene compound according to [1], wherein oxidation of the aniline compound to the nitrobenzene compound is conducted in the presence of a solvent.

[4] The method for producing a nitrobenzene compound according to [3], wherein the solvent is water, an alcohol, a nitrile, an aromatic hydrocarbon, or a mixed solvent thereof.

[5] The method for producing a nitrobenzene compound according to [3], wherein the solvent is water.

[6] The method for producing a nitrobenzene compound according to [3], wherein the solvent is a mixed solvent of water and an aromatic hydrocarbon, and the oxidation of the aniline compound to the nitrobenzene compound is conducted in the presence of a phase transfer catalyst.

[7] The method for producing a nitrobenzene compound according to [6], wherein the aromatic hydrocarbon is one or more kind selected from benzene, chlorobenzene, dichlorobenzene, trichlorobenzene, toluene, xylene, mesitylene, or ethylbenzene.

[8] The method for producing a nitrobenzene compound according to [1], wherein an aniline compound in which either one of $R^4$ or $R^5$ in general formula (1) is a C1 to C4 alkoxycarbonyl group is produced by esterification of an aminobenzoic acid compound represented by general formula (4):

[Formula 4]

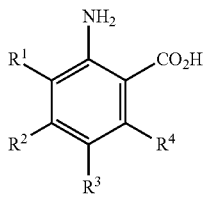

(4)

(wherein $R^1$, $R^2$, $R^3$, and $R^4$ are the same as described above.) which is obtained by amination of a halogenobenzoic acid compound represented by general formula (3):

[Formula 3]

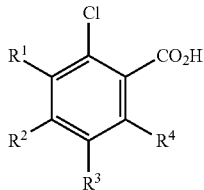

(3)

(wherein $R^1$, $R^2$, $R^3$, and $R^4$ are the same as described above).

[9] The method for producing a nitrobenzene compound according to [1], wherein the tungsten compound is tungstic acid.

[10] The method for producing a nitrobenzene compound according to [1], wherein the tungsten compound is a tungstic acid salt.

[11] The method for producing a nitrobenzene compound according to [1], wherein the tungsten compound is metal tungsten.

[12] The method for producing a nitrobenzene compound according to [6], wherein the phase transfer catalyst is a quaternary ammonium salt.

[13] The method for producing a nitrobenzene compound according to [12], wherein the phase transfer catalyst is one or more kind selected from tetrabutylammonium bromide, tetrabutylammonium hydrogen sulfate, trioctylmethylammonium chloride, or myristyltrimethylammonium bromide.

[14] The method for producing a nitrobenzene compound according to [1], wherein a pH condition under the acidic condition is pH 2.0 or less.

[15] The method for producing a nitrobenzene compound according to [1], wherein a pH condition under the neutral to alkaline condition is pH 6.5 to 16.0.

[16] The method for producing a nitrobenzene compound according to [1], wherein a pH condition under the neutral to alkaline condition is pH 6.5 to 15.0.

[17] The method for producing a nitrobenzene compound according to [1], wherein $R^2$, $R^3$, and $R^4$ in general formula (1) are each a hydrogen atom.

[18] The method for producing a nitrobenzene compound according to [1], wherein $R^1$ and $R^5$ in general formula (1) are the same or different, and each is a halogen atom or a C1 to C4 alkoxycarbonyl group.

[19] The method for producing a nitrobenzene compound according to [1], wherein $R^1$ and $R^5$ in general formula (1) are each a halogen atom.

[20] The method for producing a nitrobenzene compound according to [1], wherein $R^1$ in general formula (1) is a halogen atom and $R^5$ is a C1 to C4 alkoxycarbonyl group.

[21] The method for producing a nitrobenzene compound according to [3], wherein $R^1$ and $R^5$ in general formula (1) are each a halogen atom, $R^2$, $R^3$, and $R^4$ are each a hydrogen atom, the tungsten compound is a tungstic acid salt, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[22] The method for producing a nitrobenzene compound according to [3], wherein $R^1$ in general formula (1) is a halogen atom, $R^5$ is a C1 to C4 alkoxycarbonyl group, $R^2$, $R^3$, and $R^4$ are each a hydrogen atom, the tungsten compound is a tungstic acid salt, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[23] The method for producing a nitrobenzene compound according to [3], wherein $R^4$ and $R^5$ in general formula (1) are each a halogen atom, $R^2$, $R^3$, and $R^4$ are each a hydrogen atom, the tungsten compound is tungstic acid, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[24] The method for producing a nitrobenzene compound according to [3], wherein $R^1$ in general formula (1) is a halogen atom, $R^5$ is a C1 to C4 alkoxycarbonyl group, $R^2$, $R^3$, and $R^4$ are each a hydrogen atom, the tungsten compound is tungstic acid, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[25] The method for producing a nitrobenzene compound according to [3], wherein $R^1$ and $R^5$ in general formula (1) are each a halogen atom, $R^2$, $R^3$, and $R^4$ are each a hydrogen atom, the tungsten compound is metal tungsten, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[26] The method for producing a nitrobenzene compound according to [3], wherein $R^1$ in general formula (1) is a halogen atom, $R^5$ is a C1 to C4 alkoxycarbonyl group, $R^2$, $R^3$, and $R^4$ are each a hydrogen atom, the tungsten compound is metal tungsten, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[27] The method for producing a nitrobenzene compound according to [8], wherein $R^1$ in general formula (1) is a halogen atom, $R^5$ is a C1 to C4 alkoxycarbonyl group, $R^2$, $R^3$, and $R^4$ are each a hydrogen atom, the tungsten compound is a tungstic acid salt, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[28] The method for producing a nitrobenzene compound according to [8], wherein $R^1$ in general formula (1) is a halogen atom, $R^5$ is a C1 to C4 alkoxycarbonyl group, $R^2$, $R^3$, and $R^4$ are each a hydrogen atom, the tungsten compound is tungstic acid, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

[29] The method for producing a nitrobenzene compound according to [8], wherein $R^1$ in general formula (1) is a halogen atom, $R^5$ is a C1 to C4 alkoxycarbonyl group, $R^2$, $R^3$, and $R^4$ are each a hydrogen atom, the tungsten compound is metal tungsten, a pH condition under the acidic condition is pH 2.0 or less, a pH condition under the neutral to alkaline condition is pH 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidation reaction is conducted in the presence of a phase transfer catalyst, and the phase transfer catalyst is one or more kind selected from tetrabutylammonium bromide, tetrabutylammonium hydrogen sulfate, trioctylmethylammonium chloride, or myristyltrimethylammonium bromide.

According to the method of the present invention, a novel industrial production method for the nitrobenzene compound represented by general formula (2), useful as an intermediate for the synthesis of various organic compounds, is provided. According to the method of the present invention, the reaction can be completed using the aniline compound represented by general formula (1) as the raw material, using hydrogen peroxide, which is inexpensive, becomes harmless water after a reaction, and attracts attention as a clean and excellent oxidant, further using a tungsten compound, which is industrially easily available and inexpensive, and even without using high concentration hydrogen peroxide, which is difficult to handle and is hazardous.

In addition, in the method of the present invention, the nitrobenzene compound can be produced under mild conditions even without using a high risk organic peroxy acid such as peracetic acid or trifluoroperacetic acid.

Further, in the method of the present invention, the production of nitrobenzene compound can be simply implemented on an industrial scale with high yield and efficiency. Therefore, the method of the present invention is simple, has high safety, and is inexpensive, and therefore has a high industrial utility value.

Further, as the acid used to provide the acidic condition, it is not necessary to use phosphoric acid or the like, which may cause significant problems in environmental pollution, and the reaction can be conducted using hydrochloric acid, sulfuric acid, or hydrobromic acid, a waste liquid of which does not cause problems with the environment when merely neutralized with sodium hydroxide or the like.

DETAILED DESCRIPTION OF THE INVENTION

The present invention will be described in detail below.

The method of the present invention is a method for producing a nitrobenzene compound represented by general formula (2), comprising oxidizing an aniline compound represented by general formula (1) with hydrogen peroxide in the presence of a tungsten compound under an acidic condition, followed by oxidation with hydrogen peroxide under a neutral to alkaline condition. The production method is preferably conducted in the presence of a solvent, and a phase transfer catalyst can also be used as required.

(Raw Material Compound)

First, the aniline compound that is a raw material compound represented by general formula (1) described above, used as a raw material in the method of the present invention, will be described.

In general formula (1), $R^1$ and $R^5$ are, for example, the same or different, and each is a halogen atom consisting of a fluorine atom, a chlorine atom, a bromine atom, or an iodine atom; a C1 to C4 alkyl group such as a methyl group, an ethyl group, a propyl group, an isopropyl group, a butyl group, an isobutyl group, a sec-butyl group, or a tert-butyl group; a C1 to C4 alkoxy group such as a methoxy group, an ethoxy group, a propoxy group, an isopropoxy group, a butoxy group, an isobutoxy group, a sec-butoxy group, or a tert-butoxy group; a C1 to C4 alkoxycarbonyl group such as a methoxycarbonyl group, an ethoxycarbonyl group, a propoxycarbonyl group, or a butoxycarbonyl group; or a C1 to C4 alkoxy C1 to C4 alkyl group such as a methoxymethyl group, a methoxyethyl group, a methoxypropyl group, a methoxybutyl group, an ethoxymethyl group, a propoxymethyl group, or a butoxymethyl group; $R^2$, $R^3$, and $R^4$ are, for example, the same or different, and each is a hydrogen atom; a halogen atom consisting of a fluorine atom, a chlorine atom, a bromine atom, or an iodine atom; a C1 to C4 alkyl group such as a methyl group, an ethyl group, a propyl group, an isopropyl group, a butyl group, an isobutyl group, a sec-butyl group, or a tert-butyl group; a C1 to C4 alkoxy group such as a methoxy group, an ethoxy group, a propoxy group, an isopropoxy group, a butoxy group, an isobutoxy group, a sec-butoxy group, or a tert-butoxy group; or a C1 to C4 haloalkyl group such as a trifluoromethyl group, a difluoromethyl group, a fluoromethyl group, a 2,2,2-trifluoroethyl group, a 1,1,2,2,2-pentafluoroethyl group, a 3,3,3-trifluoropropyl group, or a 4,4,4-trifluorobutyl group.

For example, "C1 to C4" means that the number of carbon atoms of a substituent following this is 1 to 4, and the same applies hereinafter.

Specific examples of the aniline compound represented by general formula (1) that can be used in this reaction include 2,6-dichloroaniline, 2,6-dibromoaniline, 2,6-difluoroaniline, 2-chloro-6-fluoroaniline, 2-bromo-6-chloroaniline, 2-chloro-6-iodoaniline, 2,3,6-trichloroaniline, 2,4,6-trichloroaniline, 2,4,6-trimethylaniline, 2,4,6-trimethoxyaniline, 2,4,6-trifluoroaniline, 2,4,6-tribromoaniline, 2,6-dichloro-4-methoxyaniline, 2,6-dichloro-4-ethoxyaniline, 2,6-dichloro-4-propoxyaniline, 2,6-dichloro-4-butoxyaniline, 2,6-dichloro-4-methylaniline, 2,6-dichloro-4-ethylaniline, 2,6-dichloro-4-propylaniline, 2,6-dichloro-4-butylaniline, 2,3,5,6-tetrachloroaniline, methyl 2-amino-3-chlorobenzoate, ethyl 2-amino-3-chlorobenzoate, propyl 2-amino-3-chlorobenzoate, isopropyl 2-amino-3-chlorobenzoate, butyl 2-amino-3-chlorobenzoate, isobutyl 2-amino-3-chlorobenzoate, sec-butyl 2-amino-3-chlorobenzoate, tert-butyl 2-amino-3-chlorobenzoate, methyl 2-amino-3-fluorobenzoate, ethyl 2-amino-3-fluorobenzoate, methyl 2-amino-3-bromobenzoate, ethyl 2-amino-3-bromobenzoate, 2-chloro-6-methylaniline, 2-chloro-6-ethylaniline, 2-chloro-6-propylaniline, 2-chloro-6-butylaniline, 2-bromo-6-methylaniline, 2-fluoro-6-methylaniline, 2,6-dimethylaniline, 2,6-diethylaniline, 2-chloro-6-methoxyaniline, 2-chloro-6-ethoxyaniline, 2-chloro-6-propoxyaniline, 2-chloro-6-butoxyaniline, 2-chloro-6-methoxymethylaniline, 2-chloro-6-(2-methoxyethyl)aniline, 2-chloro-6-(3-methoxypropyl)aniline, 2-chloro-6-(4-methoxybutyl)aniline, 2-chloro-6-ethoxymethylaniline, 2-chloro-6-propoxymethylaniline, 2-butoxymethyl-6-chloroaniline, methyl 2-amino-3,5-dichlorobenzoate, or ethyl 2-amino-3,5-dichlorobenzoate. The above aniline compounds may be salts, for example, with acids such as hydrochloric acid and sulfuric acid and the like.

The aniline compound represented by general formula (1) is a known compound, or a compound that can be produced from a known compound by a known method. In addition, it is difficult to convert a 2,6-disubstituted aniline compound, which is included in the aniline compound above-mentioned, into a corresponding 2,6-disubstituted nitrobenzene compound under mild conditions, as already described.

(Tungsten Compound)

Examples of the tungsten compound to be used in the method of the present invention include tungstic acid salt such as sodium tungstate, sodium tungstate dihydrate, sodium tungstate decahydrate, potassium tungstate, calcium tungstate, or ammonium tungstate; tungstic acid, metal tungsten, or tungsten carbide.

For the molar ratio of the tungsten compound to be used, the range of generally 0.001 to 1.0 mole, preferably 0.005 to 0.3 moles, with respect to 1 mole of the aniline compound represented by general formula (1), can be mentioned as examples.

(Acidic Condition)

In the method of the present invention, first, the aniline compound is oxidized under an acidic condition. At this time, a high acidic condition is preferable, and the pH range of 2.0 or less can be mentioned as examples.

In order to provide a high acidic condition, an acid is added to the reaction system. Examples of the acid that can be used include sulfuric acid, hydrochloric acid, or hydrobromic acid. From the viewpoint of availability, the ease of handling, reactivity, price, safety and the like, sulfuric acid or hydrochloric acid is preferable, and sulfuric acid is further preferable.

When tungstic acid is used as the tungsten compound, the desired acidic condition is provided by the sufficiently high acidity of the tungstic acid, and therefore, it is not always necessary to add an acid other than tungstic acid. However, it may be added. When a tungstic acid salt, metal tungsten, or tungsten carbide is used as the tungsten compound, it is necessary to add an acid.

In addition, for the molar ratio of the acid to be used when the tungstic acid is not adopted for the tungsten compound, the range of generally 1.5 to 100.0 moles, preferably 2.0 to 50.0 moles, with respect to 1 mole of the tungsten compound used, can be mentioned as examples. For the molar ratio of the acid to be used when the tungsten compound is tungstic acid, the range of generally 0.0 to 100.0 moles, preferably 0.0 to 50.0 moles, with respect to 1 mole of the tungsten compound used, can be mentioned as examples.

(Phase Transfer Catalyst)

In the method of the present invention, a phase transfer catalyst can also be used as required. This phase transfer catalyst includes quaternary ammonium salts such as tetramethylammonium chloride, tetramethylammonium bromide, tetraethylammonium chloride, tetraethylammonium bromide, tetrabutylammonium chloride, tetrabutylammonium bromide, tetrabutylammonium iodide, tetrabutylammonium hydroxide, tetrabutylammonium hydrogen sulfate, trimethylbenzylammonium chloride, trimethylbenzylammonium bromide, trimethylbenzylammonium hydroxide, triethylbenzylammonium chloride, triethylbenzylammonium bromide, lauryltrimethylammonium chloride, lauryltrimethylammonium bromide, benzyllauryldimethylammonium chloride, benzyllauryldimethylammonium bromide, trioctylmethylammonium chloride, trioctylmethylammonium bromide, trioctylmethylammonium chloride, trioctylmethylammonium bromide, benzyldimethyloctadecylammonium chloride, benzyldimethyloctadecylammonium bromide, benzyllauryldimethylammonium chloride, myristyltrimethylammonium bromide, or benzyllauryldimethylammonium bromide; crown ethers such as 12-crown-4, 15-crown-5, or 18-crown-6; and phosphonium salts such as tetra n-butylphosphonium bromide, tetraphenylphosphonium bromide, or tetraoctylphosphonium bromide. Preferable examples include quaternary ammonium salts such as tetrabutylammonium bromide, tetrabutylammonium hydrogen sulfate, trimethylbenzylammonium chloride, trimethylbenzylammonium bromide, trioctylmethylammonium chloride, benzyllauryldimethylammonium chloride, trioctylmethylammonium bromide, benzyldimethyloctadecylammonium chloride, benzyldimethyloctadecylammonium bromide, or myristyltrimethylammonium bromide.

For the molar ratio of the phase transfer catalyst to be used, the range of generally 0.001 to 0.5 moles, preferably 0.005 to 0.3 moles, with respect to 1 mole of the aniline compound, can be mentioned as examples.

(Neutral to Alkaline Condition)

In the method of the present invention, the aniline compound represented by general formula (1) is further oxidized with hydrogen peroxide under a neutral to alkaline condition following the oxidation under the acidic condition. For this neutral to alkaline condition, the pH range of 6.0 or more, preferably the range of 6.5 to 16.0, and further preferably the range of 6.5 to 15.0 is mentioned.

(Base) Therefore, in the method of the present invention, a base is used to make the system under the acidic condition alkaline. This base includes alkali metal hydroxides or alkaline-earth metal hydroxides such as sodium hydroxide, potassium hydroxide, lithium hydroxide, or calcium hydroxide; alkali metal carbonates or alkaline-earth metal carbonates such as sodium carbonate, potassium carbonate, calcium carbonate, or magnesium carbonate; alkali metal hydrogen carbonates or alkaline-earth metal hydrogen carbonates such as sodium hydrogen carbonate, potassium hydrogen carbonate, or calcium hydrogen carbonate; carboxylates such as alkali metal acetates or alkaline-earth metal acetates (e.g., sodium acetate, potassium acetate, calcium acetate, or magnesium acetate); and organic bases such as triethylamine, pyridine, or 1,8-diazabicyclo[5.4.0]-7-undecene.

For the amount of the base to be used, in addition to an equivalent of the base required for neutralization, with respect to the amount of the above acid such as sulfuric acid, hydrochloric acid, hydrobromic acid, or tungstic acid used for the oxidation under the acidic condition, an excess of the base is further added. For the molar ratio of the excess base used, the range of generally 0.01 to 10.0 moles, preferably 0.1 to 5.0 moles, with respect to 1 mole of the aniline compound, can be mentioned as examples. In addition, the neutralization refers to a state in which the pH value is in the range of 6.0 to 8.0.

(Method for Confirming Disappearance of Aniline Compound)

In the method of the present invention, oxidation is further conducted under a neutral to alkaline condition following the oxidation under an acidic condition, as described above. For this, it is preferable to confirm the state of the remaining aniline compound, and it is simple to conduct this confirmation by gas chromatography analysis and HPLC analysis. The analysis may be any of analysis by the area percentage, analysis by the absolute calibration method, analysis by the internal standard method, or the like. Cases where the aniline compound used for the raw material is generally in the range of 0 to 10%, preferably 0 to 5%, and further preferably 0 to 3%, in the analysis may be determined as "the disappearance of the aniline compound."

(Hydrogen Peroxide)

In the method of the present invention, both the oxidation of the aniline compound represented by general formula (1) under the acidic condition and the oxidation under the neutral to alkaline condition are conducted with hydrogen peroxide. The concentration of the hydrogen peroxide is not particularly limited, and is practically less than 60%, preferably less than 45%, considering volume efficiency, the safety aspect and the like. For the hydrogen peroxide solution, a commercially available hydrogen peroxide can be generally used as it is, or after concentration adjustment is conducted by dilution, concentration, or the like as required.

The method for adding hydrogen peroxide is not particularly limited. Examples of the method include a method of adding hydrogen peroxide simultaneously with the aniline compound represented by general formula (1), and a method of adding hydrogen peroxide in the presence of the aniline compound represented by general formula (1), and further include a method of adding the total amount of hydrogen peroxide required for the oxidation of the aniline compound represented by general formula (1) to the nitrobenzene compound represented by general formula (2) under the acidic condition, and a method of adding hydrogen peroxide separately under the acidic condition and under the neutral to alkaline condition.

For the molar ratio of hydrogen peroxide to be used when the total amount of hydrogen peroxide is added under the acidic condition first, the range of generally 3.0 to 14.0 moles, preferably 3.0 to 9.0 moles with respect to 1 mole of the aniline compound represented by general formula (1) can be mentioned as examples. For the molar ratio of hydrogen peroxide to be used when hydrogen peroxide is added separately under the acidic condition and under the neutral to alkaline condition, the range of generally 2.0 to 8.0 moles, preferably 2.0 to 5.0 moles with respect to 1 mole of the aniline compound represented by general formula (1) under the acidic condition, and the range of generally 1.0 to 6.0 moles, preferably 1.0 to 4.0 moles with respect to 1 mole of the aniline compound represented by general formula (1) under the neutral to alkaline condition, can be mentioned as examples. In other words, hydrogen peroxide may be added both in the oxidation under the acidic condition and the oxidation under the neutral to alkaline condition, or the total amount of hydrogen peroxide required may be added in the oxidation under the acidic condition.

(High Concentration Hydrogen Peroxide)

For the "high concentration hydrogen peroxide" used in the conventional art above-mentioned, hydrogen peroxide generally at a concentration of 45% or more, more limitedly 60% or more, can be mentioned as examples.

(Solvent)

In the method of the present invention, both the oxidation under the acidic condition and the oxidation under the neutral to alkaline condition can be carried out without a solvent. However, in order to allow the reaction to proceed smoothly, a solvent is preferably used. The "solvent" in the method of the present invention also includes one that forms a suspension when a reagent is added.

The solvent that can be used in this reaction include alcohols such as methanol, ethanol, isopropyl alcohol, n-propyl alcohol, or t-butyl alcohol; nitriles such as acetonitrile or propionitrile; ketones such as acetone, methyl ethyl ketone, methyl isopropyl ketone, or methyl isobutyl ketone (MIBK); ethers such as tetrahydrofuran, dioxane, diethyl ether, or methyl-t-butyl ether; halogenated hydrocarbons such as dichloromethane, chloroform, or carbon tetrachloride; aromatic hydrocarbons such as benzene, chlorobenzene, dichlorobenzene, trichlorobenzene, toluene, xylene, mesitylene, or ethylbenzene; amides such as N,N-dimethylformamide or N,N-dimethylacetamide; sulfur compounds such as dimethyl sulfoxide; and water. The solvent can be used singly, or as a mixed solvent in any mixing ratio. Preferable examples include alcohols such as methanol, ethanol, isopropyl alcohol, n-propyl alcohol, or t-butyl alcohol; aromatic hydrocarbons such as benzene, chlorobenzene, dichlorobenzene, trichlorobenzene, toluene, xylene, mesitylene, or ethylbenzene; and water. Further preferable examples include methanol and a mixed solvent of water and one or more kind selected from benzene, chlorobenzene, dichlorobenzene, trichlorobenzene, toluene, xylene, mesitylene, or ethylbenzene, in terms of price, safety, and yield.

The amount of the solvent is preferably an amount that allows for sufficient stirring of the reaction system. For example, the range of generally 10.0 L (liters) or less, further preferably 0.01 to 3.0 L, with respect to 1 mole of the raw material compound represented by general formula (1), can be mentioned as examples.

(Reaction Conditions Under Acidic Condition)

For the reaction temperature of this reaction, generally the range of −20° C. to 90° C. can be mentioned as examples. Preferably the range of −10° C. to 80° C., further preferably the range of 0° C. to 70° C. can be mentioned as examples.

The reaction time of this reaction is not particularly limited. The reaction time is generally 0.5 hours to 36 hours, preferably 1 hour to 24 hours from the viewpoint of by-product suppression and the like.

(Reaction Conditions Under Neutral to Alkaline Condition)

For the reaction temperature of this reaction, generally the range of −20° C. to 95° C. can be mentioned as examples. Preferably, the range of −10° C. to 90° C., further preferably the range of 0° C. to 85° C. can be mentioned. The above tungsten compound is not required for the oxidation under the reaction conditions. However, the reaction proceeds even if the tungsten compound is present in the reaction system.

The reaction time of this reaction is not particularly limited. The reaction time is generally 0.2 hours to 36 hours, preferably 0.5 hours to 24 hours from the viewpoint of by-product suppression and the like.

According to this reaction, the nitrobenzene compound represented by general formula (2) is produced with high yield under mild conditions without using a special reaction apparatus.

(Yield)

In the method of the present invention, the yield of the target product is preferably 60% or more, more preferably 62 to 98%, and further preferably 70 to 98% (particularly preferably 80 to 98%).

This yield can be calculated from the number of moles of the nitrobenzene compound that is the target material to be obtained with respect to the number of moles of the aniline compound represented by general formula (1) that is the raw material. In other words, the yield in the present invention is represented by the following equation.

yield(%)=100×{(the number of moles of the obtained target material)/(the number of moles of the raw material)}

In Examples 1 to 3 described later, 1 mole of a nitrobenzene compound can be theoretically produced from 1 mole of an aniline compound of general formula (1), the raw material. Therefore, the actual yield can be calculated from this theoretical value.

On the other hand, an aniline compound in which either one of $R^1$ or $R^5$ in the aniline compound represented by general formula (1) is a C1 to C4 alkoxycarbonyl group can be produced as follows.

(Method for Producing Aminobenzoic Acid Compound by Amination)

In the production method, first, a halogenobenzoic acid compound represented by general formula (3):

[Formula 5]

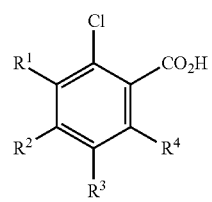

(3)

(wherein $R^1$, $R^2$, $R^3$, and $R^4$ are the same as described above.) is reacted with ammonia in the presence of copper halide or copper oxide using a base or a high pressure reactor as required, to aminate the halogenobenzoic acid compound to produce an aminobenzoic acid compound represented by general formula (4):

[Formula 6]

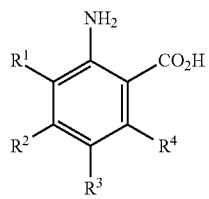

(4)

(Halogenobenzoic Acid Compound)

In the halogenobenzoic acid compound represented by general formula (3) that can be used in this reaction, $R^1$, $R^2$, $R^3$, and $R^4$ are the same as those in the above aniline compound represented by general formula (1). Therefore, specific examples of this compound include 2,3-dichlorobenzoic acid, 2-chloro-3-fluorobenzoic acid, 2,3,5-trichlorobenzoic acid, 2-chloro-3-methylbenzoic acid, and 2,3-dibromobenzoic acid. The halogenobenzoic acid compound represented by general formula (3) is a known compound, or a compound that can be produced from a known compound by a known method.

(Copper Halide)

The copper halide to be used for the amination of the halogenobenzoic acid compound represented by general formula (3) includes cuprous(I) chloride, cupric(II) chloride, cuprous(I) bromide, and cupric(II) bromide.

Regarding the molar ratio of the copper halide to be used in this reaction, the reaction can proceed in any molar ratio with respect to that of the raw material compound represented by the general formula (3). The range of generally 0.01 to 0.5 moles, preferably 0.05 to 0.2 moles, with respect to 1 mole of the halogenobenzoic acid compound represented by general formula (3) (raw material compound), can be mentioned as examples.

(Copper Oxide)

The copper oxide to be used for the amination of the halogenobenzoic acid compound represented by general formula (3) includes cuprous(I) oxide and cupric(II) oxide.

Regarding the molar ratio of the copper oxide to be used in this reaction, the reaction can proceed in any molar ratio with respect to that of the raw material compound represented by the general formula (3). The range of generally 0.01 to 0.5 moles, preferably 0.05 to 0.2 moles, with respect to 1 mole of the halogenobenzoic acid compound represented by general formula (3) (raw material compound), can be mentioned as examples.

(Solvent)

This reaction can be carried out even without a solvent. However, in order to allow the reaction to proceed smoothly, a solvent is preferably used.

The solvent that can be used in this reaction includes alcohols such as methanol, ethanol, isopropyl alcohol, n-propyl alcohol, and t-butyl alcohol; nitriles such as acetonitrile and propionitrile; ethers such as tetrahydrofuran, dioxane, diethyl ether, and methyl-t-butyl ether; halogenated hydrocarbons such as dichloromethane, chloroform, and carbon tetrachloride; aromatic hydrocarbons such as benzene, chlorobenzene, nitrobenzene, and toluene; amides such as N,N-dimethylformamide and N,N-dimethylacetamide; sulfur compounds such as dimethyl sulfoxide; and water. The solvent can be used singly, or as a mixed solvent in any mixing ratio.

The amount of the solvent to be used is generally in the range of 10.0 L (liters) or less, further preferably 0.01 to 3.0 L, with respect to 1 mole of the raw material compound represented by formula (3).

As the reaction temperature of this reaction, generally, the range of −30° C. to 200° C. can be mentioned as examples. The range is preferably −10° C. to 150° C.

The reaction time of this reaction is not particularly limited. The reaction time is generally 0.5 hours to 48 hours, preferably 1 hour to 36 hours from the viewpoint of by-product suppression and the like.

(Ammonia)

As the ammonia, ammonia solutions with water, alcohols and the like, or an ammonia gas can be mentioned, for example.

The concentration of the ammonia solution is not particularly limited, and is practically 30% or less, considering volume efficiency the safety aspect and the like. For the ammonia solution, a commercially available ammonia solution is generally used as it is, or after concentration adjustment is conducted by dilution, concentration, or the like as required.

Regarding the molar ratio of the ammonia solution to be used in this reaction, the reaction can proceed in any molar ratio with respect to that of the raw material compound represented by the general formula (3). The range of generally 2.0 to 30.0 moles, preferably 2.0 to 15.0 moles, with respect to 1 mole of the halogenobenzoic acid compound represented by general formula (3) (raw material compound), can be mentioned as examples.

For the ammonia, ammonia commercially available as liquefied ammonia is generally used as it is, or ammonia generated by adding ammonia water to sodium hydroxide or potassium hydroxide is used.

Regarding the molar ratio of the ammonia gas to be used in this reaction, the reaction can proceed in any molar ratio with respect to that of the raw material compound represented by the general formula (3). The range of generally 2.0 to 30.0 moles, preferably 2.0 to 15.0 moles, with respect to 1 mole of the halogenobenzoic acid compound represented by general formula (3) (raw material compound), can be mentioned as examples.

(Base) In order to react the halogenobenzoic acid compound represented by general formula (3) with ammonia, a base can be used. This base includes alkali metal hydroxides or alkaline-earth metal hydroxides such as sodium hydroxide, potassium hydroxide, lithium hydroxide, or calcium hydroxide; alkali metal carbonates or alkaline-earth metal carbonates such as sodium carbonate, potassium carbonate, calcium carbonate, or magnesium carbonate; alkali metal hydrogen carbonates or alkaline-earth metal hydrogen carbonates such as sodium hydrogen carbonate, potassium hydrogen carbonate, or calcium hydrogen carbonate; and carboxylates such as alkali metal acetates or alkaline-earth metal acetates (e.g., sodium acetate, potassium acetate, calcium acetate, or magnesium acetate).

For the molar ratio of the base to be used in this reaction, the range of generally 0.1 to 10.0 moles, preferably 0.1 to 5.0 moles, with respect to 1 mole of the halogenobenzoic acid compound (raw material compound), can be mentioned as examples.

(High Pressure Reactor)

In order to react the halogenobenzoic acid compound represented by general formula (3) with ammonia, a high pressure reactor can be used. For this high pressure reactor, 10 mL to 3 L sealed tubes are laboratorially used, and 50 L to 20000 L high pressure reactors are industrially used.

For the pressure in the high pressure reactor, the range of generally 1 to 100 atmospheres, preferably 2 to 50 atmospheres, can be mentioned as examples.

(Yield)

In the present invention, the yield of the target product is preferably 60% or more, more preferably 63 to 95%, and further preferably 67 to 95% (particularly preferably 70 to 95%).

This yield can be calculated from the number of moles of the aminobenzoic acid compound that is the intermediate to be obtained with respect to the number of moles of the halogenobenzoic acid compound represented by general formula (3) that is the raw material. In other words, the yield in the present invention is represented by the following equation.

yield(%)=100×{(the number of moles of the obtained target material)/(the number of moles of the raw material)}

In Examples 4 and 5 described later, 1 mole of an aminobenzoic acid compound can be theoretically produced from 1 mole of a halogenobenzoic acid compound of general formula (3), the raw material. Therefore, the actual yield can be calculated from this theoretical value.

According to this reaction, the aminobenzoic acid compound represented by general formula (4) is produced with high yield. The obtained aminobenzoic acid compound represented by general formula (4) is used as an intermediate raw material of the aniline compound (aminobenzoate compound) in which either one of $R^1$ or $R^5$ in the aniline compound represented by general formula (1) is a C1 to C4 alkoxycarbonyl group, by being treated for isolation, or without isolation.

(Method for Producing Aminobenzoate Compound by Esterification)

In this production method, then, the aminobenzoic acid compound represented by general formula (4) is reacted in the presence of an alkylating agent and a base, and in the presence of a phase transfer catalyst as required, or reacted in the presence of an alcohol by adding an acid catalyst, or reacted with a chlorosulfite obtained by preparation with an alcohol and thionyl chloride, in the presence of a base as required, to produce the aniline compound (aminobenzoate compound) in which either one of $R^1$ or $R^5$ in the aniline compound represented by general formula (1) is a C1 to C4 alkoxycarbonyl group.

(Aminobenzoic Acid Compound)

In this aminobenzoic acid compound represented by general formula (4) that can be used in this reaction, $R^1$, $R^2$, $R^3$, and $R^4$ are the same as those in the above aniline compound represented by general formula (1). Therefore, specific examples of this compound include 2-amino-3-chlorobenzoic acid, 2-amino-3-fluorobenzoic acid, 2-amino-3,5-dichlorobenzoic acid, 2-amino-3-methylbenzoic acid, and 2-amino-3-bromobenzoic acid. These compounds are compounds that are known, or can be produced by the above method.

(Production Method Conducted in Presence of Alkylating Agent and Base)

In the production method, the aminobenzoic acid compound represented by general formula (4) is reacted in the presence of an alkylating agent and a base, and in the presence of a phase transfer catalyst as required, to produce the target aminobenzoate compound.

(Alkylating Agent)

The alkylating agent includes dialkyl sulfates such as dimethyl sulfate and diethyl sulfate, and alkyl halides such as methyl iodide, ethyl iodide, and ethyl bromide.

For the molar ratio of the alkylating agent to be used, the range of generally 1.0 to 6.0 moles, preferably 1.0 to 3.0 moles, with respect to 1 mole of the aminobenzoic acid compound represented by general formula (4) (raw material compound), can be mentioned as examples.

(Base) The base includes alkali metal hydroxides or alkaline-earth metal hydroxides such as sodium hydroxide, potassium hydroxide, lithium hydroxide, or calcium hydroxide; alkali metal carbonates or alkaline-earth metal carbonates such as sodium carbonate, potassium carbonate, calcium carbonate, or magnesium carbonate; alkali metal hydrogen carbonates or alkaline-earth metal hydrogen carbonates such as sodium hydrogen carbonate, potassium hydrogen carbonate, or calcium hydrogen carbonate; carboxylates such as alkali metal acetates or alkaline-earth metal acetates (e.g., sodium acetate, potassium acetate, calcium acetate, or magnesium acetate); and organic bases such as triethylamine, pyridine, or 1,8-diazabicyclo[5.4.0]-7-undecene.

For the molar ratio of the base to be used, the range of generally 1.0 to 6.0 moles, preferably 1.0 to 3.0 moles, with respect to 1 mole of the aminobenzoic acid compound, can be mentioned as examples.

(Phase Transfer Catalyst)

The phase transfer catalyst to be used as required includes quaternary ammonium salts such as tetramethylammonium chloride, tetramethylammonium bromide, tetraethylammonium chloride, tetraethylammonium bromide, tetrabutylammonium chloride, tetrabutylammonium bromide, tetrabutylammonium iodide, tetrabutylammonium hydroxide, tetrabutylammonium hydrogen sulfate, trimethylbenzylammonium chloride, trimethylbenzylammonium bromide, trimethylbenzylammonium hydroxide, triethylbenzylammonium chloride, triethylbenzylammonium bromide, lauryltrimethylammonium chloride, lauryltrimethylammonium bromide, benzyllauryldimethylammonium chloride, benzyllauryldimethylammonium bromide, trioctylmethylammonium chloride, trioctylmethylammonium bromide, trioctylmethylammonium chloride, trioctylethylammonium bromide, benzyldimethyloctadecylammonium chloride, benzyldimethyloctadecylammonium bromide, benzyllauryldimethylammonium chloride, myristyltrimethylammonium bromide, or benzyllauryldimethylammonium bromide; crown ethers such as 12-crown-4, 15-crown-5, or 18-crown-6; and phosphonium salts such as tetra n-butylphosphonium bromide, tetraphenylphosphonium bromide, or tetraoctylphosphonium bromide. Preferable examples include quaternary ammonium salts such as tetrabutylammonium bromide, tetrabutylammonium hydrogen sulfate, trimethylbenzylammonium chloride, trimethylbenzylammonium bromide, trioctylmethylammonium chloride, benzyllauryldimethylammonium chloride, trioctylmethylammonium bromide, benzyldimethyloctadecylammonium chloride, benzyldimethyloctadecylammonium bromide, or myristyltrimethylammonium bromide.

For the molar ratio of the phase transfer catalyst to be used as required, the range of generally 0.001 to 0.5 moles, preferably 0.005 to 0.2 moles, with respect to mole of the aminobenzoic acid compound, can be mentioned as examples.

(Solvent)

This reaction can be carried out even without a solvent. However, in order to allow the reaction to proceed smoothly, a solvent is preferably used.

The solvent that can be used in this reaction includes ketones such as acetone, methyl ethyl ketone, methyl isopropyl ketone, and methyl isobutyl ketone (MIBK); ethers such as tetrahydrofuran, dioxane, diethyl ether, and methyl-t-butyl ether; halogenated hydrocarbons such as dichloromethane, chloroform, and carbon tetrachloride; aromatic hydrocarbons such as benzene, chlorobenzene, nitrobenzene, and toluene; nitriles such as acetonitrile and propionitrile; amides such as N,N-dimethylformamide and N,N-dimethylacetamide; sulfur compounds such as dimethyl sulfoxide; and water. The solvent can be used singly, or as a mixed solvent in any mixing ratio.

The amount of the solvent to be used is generally in the range of 0.01 to 10.0 L (liters), further preferably in the range of 0.1 to 3.0 L (liters), with respect to 1 mole of the aminobenzoic acid compound represented by general formula (4) (raw material compound).

As the reaction temperature of this reaction, generally, the range of −30° C. to 100° C. can be mentioned as examples. The range is preferably −10° C. to 80° C., further preferably −10° C. to 60° C.

The reaction time of this reaction is not particularly limited. The reaction time is generally 0.5 hours to 48 hours, preferably 1 hour to 36 hours from the viewpoint of by-product suppression and the like.

(Production Method of Reacting in Presence of Alcohol by Adding Acid Catalyst)

In the production method, the aminobenzoic acid compound represented by general formula (4) is reacted in the presence of an alcohol by adding an acid catalyst to produce the target aminobenzoate compound.

(Alcohol)

As the alcohol that can be used in this reaction, methanol, ethanol, isopropyl alcohol, n-propyl alcohol, t-butyl alcohol and the like can be mentioned, for example.

The amount of the alcohol to be used is generally in the range of 0.5 to 10.0 L (liters), further preferably in the range of 1 to 5.0 L (liters), with respect to 1 mole of the aminobenzoic acid compound represented by general formula (4) (raw material compound).

(Acid Catalyst)

As the acid catalyst that can be used in this reaction, hydrogen chloride, sulfuric acid, p-toluenesulfonic acid, benzenesulfonic acid, phosphoric acid and the like can be mentioned, for example.

For the molar ratio of the acid catalyst to be used, the range of generally 0.01 to 2.0 moles, preferably 0.01 to 1.5 moles, with respect to 1 mole of the aminobenzoic acid compound represented by general formula (4) (raw material compound), can be mentioned as examples.

(Solvent)

This reaction can be carried out even with only the alcohol. However, a mixed solvent with a solvent other than the alcohol can also be used.

The solvent that can be used as the mixed solvent in this reaction includes ketones such as acetone, methyl ethyl ketone, methyl isopropyl ketone, and methyl isobutyl ketone (MIBK); ethers such as tetrahydrofuran, dioxane, diethyl ether, and methyl-t-butyl ether; halogenated hydrocarbons such as dichloromethane, chloroform, and carbon tetrachloride; aromatic hydrocarbons such as benzene, chlorobenzene, nitrobenzene, and toluene; nitriles such as acetonitrile and propionitrile; amides such as N,N-dimethylformamide and N,N-dimethylacetamide; sulfur compounds such as dimethyl sulfoxide; and water.

The amount of the solvent other than the alcohol is generally in the range of 0.01 to 10.0 L (liters), further preferably in the range of 0.1 to 3.0 L (liters), with respect to 1 mole of the aminobenzoic acid compound represented by general formula (4) (raw material compound).

As the reaction temperature of this reaction, generally, the range of −30° C. to 140° C. can be mentioned as examples. The range is preferably −10° C. to 120° C.

The reaction time of this reaction is not particularly limited. The reaction time is generally 0.5 hours to 48 hours, preferably 1 hour to 36 hours from the viewpoint of by-product suppression and the like.

(Production Method of Reacting with Chlorosulfite Prepared from Alcohol and Thionyl Chloride)

In this production method, the aminobenzoic acid compound represented by general formula (4) is reacted with a chlorosulfite obtained by preparation with an alcohol and thionyl chloride, in the presence of a base as required, to produce the target aminobenzoate compound.

(Production Method of Reacting with Chlorosulfite without Using Base)

(Preparation of Chlorosulfite)

The chlorosulfite can be obtained by reacting thionyl chloride with an alcohol.

For the molar ratio of the thionyl chloride to be used, the range of generally 1.0 to 6.0 moles, preferably 1.0 to 3.0 moles, with respect to 1 mole of the aminobenzoic acid compound represented by general formula (4) (raw material compound), can be mentioned as examples.

As the alcohol that can be used in this reaction, methanol, ethanol, isopropyl alcohol, n-propyl alcohol, t-butyl alcohol and the like can be mentioned, for example.

For the molar ratio of the alcohol to be used, the range of generally 1.0 to 6.0 moles, preferably 1.0 to 3.0 moles, with respect to 1 mole of the thionyl chloride, can be mentioned as examples. In addition, the alcohol can also be used as a solvent, and therefore, in this case, the alcohol is generally used in the range of 0.5 to 10.0 L (liters), further preferably in the range of 1.0 to 3.0 L (liters), with respect to 1 mole of the aminobenzoic acid compound of general formula (4), the raw material.

For the molar ratio of the chlorosulfite to be used, the range of generally 1.0 to 6.0 moles, preferably 1.0 to 3.0 moles, with respect to 1 mole of the aminobenzoic acid compound represented by general formula (4) (raw material compound), can be mentioned as examples. The amount of the chlorosulfite is calculated assuming that the thionyl chloride used reacts with the alcohol with a yield of 100% to produce the chlorosulfite. Here, the yield is represented by the following equation.

yield(%)=100×{(the number of moles of the obtained target material)/(the number of moles of the raw materials)}

(Solvent)

This reaction can be carried out even without a solvent. However, in order to allow the reaction to proceed smoothly, a solvent is preferably used.

The solvent that can be used in this reaction includes alcohols such as methanol, ethanol, isopropyl alcohol, n-propyl alcohol, and t-butyl alcohol; nitriles such as acetonitrile and propionitrile; ketones such as acetone, methyl ethyl ketone, methyl isopropyl ketone, and methyl isobutyl ketone; ethers such as tetrahydrofuran, dioxane, diethyl ether, and methyl-t-butyl ether; halogenated hydrocarbons such as dichloromethane, chloroform, and carbon tetrachloride; aromatic hydrocarbons such as benzene, chlorobenzene, nitrobenzene, and toluene; amides such as N,N-dimethylformamide and N,N-dimethylacetamide; and sulfur compounds such as dimethyl sulfoxide. The solvent can be used singly, or as a mixed solvent in any mixing ratio.

The amount of the solvent to be used is generally in the range of 0.01 to 10.0 L (liters), further preferably in the range of 0.01 to 3.0 L (liters), with respect to 1 mole of the aminobenzoic acid compound represented by general formula (4) (raw material compound).

As the reaction temperature of this reaction, generally, the range of −30° C. to 60° C. can be mentioned as examples. The range is preferably −20° C. to 40° C.

The reaction time of this reaction is not particularly limited. From the viewpoint of by-product suppression and the like, the reaction time is generally 0.5 hours to 24 hours, preferably 1 hour to 12 hours.

The chlorosulfite prepared in this reaction can be used without purification, for the following production method of reacting using a base.

(Production Method of Reacting with Chlorosulfite Using Base)
(Preparation of Chlorosulfite)

The chlorosulfite can be obtained by reacting thionyl chloride with an alcohol as in the case of the above reaction using no base.

For the molar ratio of the chlorosulfite to be used, the range of generally 1.0 to 6.0 moles, preferably 1.0 to 3.0 moles, with respect to 1 mole of the aminobenzoic acid compound represented by general formula (4) (raw material compound), can be mentioned as examples. The amount of the chlorosulfite is calculated assuming that the thionyl chloride used reacts with the alcohol with a yield of 100% to produce the chlorosulfite. Here, the yield is represented by the following equation.

$$\text{yield}(\%)=100\times\{(\text{the number of moles of the obtained target material})/(\text{the number of moles of the raw materials})\}$$

(Base) The base to be used as required includes alkali metal hydroxides or alkaline-earth metal hydroxides such as sodium hydroxide, potassium hydroxide, lithium hydroxide, or calcium hydroxide; alkali metal carbonates or alkaline-earth metal carbonates such as sodium carbonate, potassium carbonate, calcium carbonate, or magnesium carbonate; alkali metal hydrogen carbonates or alkaline-earth metal hydrogen carbonates such as sodium hydrogen carbonate, potassium hydrogen carbonate, or calcium hydrogen carbonate; carboxylates such as alkali metal acetates or alkaline-earth metal acetates such as sodium acetate, potassium acetate, calcium acetate, or magnesium acetate; and organic bases such as triethylamine, pyridine, or 1,8-diazabicyclo[5.4.0]-7-undecene.

For the molar ratio of the base to be used as required, the range of generally 1.0 to 5.0 moles, preferably 1.0 to 3.0 moles, with respect to 1 mole of the aminobenzoic acid compound represented by general formula (4) (raw material compound), can be mentioned as examples.

(Solvent)

This reaction can be carried out even without a solvent. However, in order to allow the reaction to proceed smoothly, a solvent is preferably used.

The solvent that can be used in this reaction includes alcohols such as methanol, ethanol, isopropyl alcohol, n-propyl alcohol, and t-butyl alcohol; nitriles such as acetonitrile and propionitrile; ketones such as acetone, methyl ethyl ketone, methyl isopropyl ketone, and methyl isobutyl ketone (MIBK); ethers such as tetrahydrofuran, dioxane, diethyl ether, and methyl-t-butyl ether; halogenated hydrocarbons such as dichloromethane, chloroform, and carbon tetrachloride; aromatic hydrocarbons such as benzene, chlorobenzene, nitrobenzene, and toluene; amides such as N,N-dimethylformamide and N,N-dimethylacetamide; and sulfur compounds such as dimethyl sulfoxide. The solvent can be used singly, or as a mixed solvent in any mixing ratio.

The amount of the solvent to be used is generally in the range of 0.01 to 10.0 L (liters), further preferably in the range of 0.01 to 3.0 L (liters), with respect to 1 mole of the raw material compound represented by formula (4).

As the reaction temperature of this reaction, generally, the range of −30° C. to 60° C. can be mentioned as examples. The range is preferably −10° C. to 40° C.

The reaction time of this reaction is not particularly limited. The reaction time is generally 0.5 hours to 24 hours, preferably 1 hour to 12 hours from the viewpoint of by-product suppression and the like.

According to this reaction, the aniline compound (aminobenzoate compound) in which either one of $R^1$ or $R^5$ in general formula (1) is a C1 to C4 alkoxycarbonyl group is produced with high yield under mild conditions without using a special reaction apparatus. The aminobenzoate compound obtained is used as an intermediate raw material of certain compound (nitrobenzoate compound) included in the nitrobenzene compound represented by general formula (2), by being treated for isolation, or without isolation.

(Yield)

In the present invention, the yield of the target product is preferably 60% or more, more preferably 61 to 99%, and further preferably 74 to 99% (particularly preferably 90 to 99%).

This yield can be calculated from the number of moles of the aminobenzoate compound that is the target material to be obtained with respect to the number of moles of the aminobenzoic acid compound represented by general formula (4) (raw material compound) that is the raw material. In other words, the yield in the present invention is represented by the following equation.

$$\text{yield}(\%)=100\times\{(\text{the number of moles of the obtained target material})/(\text{the number of moles of the raw material})\}$$

In Examples 6 to 9 described later, 1 mole of an aminobenzoate compound can be theoretically produced from 1 mole of an aminobenzoic acid compound represented by general formula (4) that is the raw material. Therefore, the actual yield can be calculated from this theoretical value.

EXAMPLES

Next, the method for producing the compound of the present invention is specifically described by giving Examples. However, the present invention is not limited in any way by these Examples.

Example 1

Production of 2,6-Dichloronitrobenzene 1.32 g (4.0 mmol) of sodium tungstate dihydrate and 4.0 g (40 mmol) of concentrated sulfuric acid were added to a solution of 16.2 g (100 mmol) of 2,6-dichloroaniline in 120 ml of methanol, and the mixture was heated to 40° C. 30 ml (291 mmol) of a 30% hydrogen peroxide solution was added dropwise over 10 hours. The pH value at this time was 0.5. After the completion of the dropwise addition, the mixture was stirred at 40° C. for 9 hours. After the disappearance of the 2,6-dichloroaniline was confirmed by gas chromatography (area percentage method), a solution of 9.8 g (150 mmol) of 86% potassium hydroxide in 24.3 ml of methanol was added dropwise while the temperature of the reaction liquid was adjusted to 40° C. or less. After the completion of the dropwise addition, the mixture was stirred at room temperature for 2 hours, and the reaction was completed. After the completion of the reaction, 95 ml of toluene and 32 ml of water were added, and the mixture was stirred for a while, and filtered. The filtrate was separated. The obtained organic phase was washed with 8 ml of water, and then heated to reflux, and dehydrated. Thus, 2,6-dichloronitrobenzene was obtained as a toluene solution. This solution was analyzed by gas chromatography by the absolute calibration method, and as a result, the yield was 92%. The amount of the potassium hydroxide added is sufficient to make the pH condition alkaline.

$^1$H-NMR (300 MHz, DMSO-d$_6$, σ): 7.36-7.47 (m, 3H)

Example 2

Production of Methyl 3-Chloro-2-nitrobenzoate

A solution of 5.3 g (16.2 mmol) of sodium tungstate dihydrate and 3.2 g (32.3 mmol) of concentrated sulfuric acid in 53 ml of methanol was heated to 40° C., and a solution of 15 g (80.8 mmol) of methyl 2-amino-3-chlorobenzoate in 13 ml of methanol, and 33.0 ml (323 mmol) of a 30% hydrogen peroxide solution were simultaneously added dropwise over 10 hours. The pH value at this time was 0.5. After the completion of the dropwise addition, the mixture was stirred at 40° C. for 2 hours. After the disappearance of the methyl 2-amino-3-chlorobenzoate was confirmed by HPLC analysis (area percentage method), 30 ml of toluene and 8.3 ml (80.8 mmol) of a 30% hydrogen peroxide solution were added to the reaction liquid, and 19.9 g (88.9 mmol) of a 25% aqueous potassium hydroxide solution was further added dropwise so that the temperature was 30° C. or less. The mixture was stirred at room temperature for 12 hours, and the reaction was completed. After the completion of the reaction, the methanol was distilled off, and 58 ml of toluene was added for separation. The obtained organic phase was washed with 20 ml of water, and methyl 3-chloro-2-nitrobenzoate was obtained as a toluene solution. This solution was analyzed by HPLC by the absolute calibration method, and as a result, the yield was 88%. The amount of the potassium hydroxide added is sufficient to make the pH condition alkaline.

$^1$H-NMR (300 MHz, DMSO-d$_6$, σ): 3.87 (S, 3H), 7.77 (dd, J=6.6, 6.6 Hz, 1H), 8.06 (dd, J=1.0, 6.6 Hz, 1H), 8.08 (dd, J=1.0, 6.6 Hz, 1H)

Example 3

Production of 2,6-Dichloronitrobenzene 0.66 g (2.64 mmol) of tungstic acid and 0.40 g (1.23 mmol) of tetrabutylammonium bromide were added to a suspension of 2.0 g (12.3 mmol) of 2,6-dichloroaniline in 6 ml of water, and the mixture was heated to 40° C. 4.9 g (43.1 mmol) of a 30% hydrogen peroxide solution was added. The pH value at this time was 1.5. Then, the mixture was stirred at 40° C. for 16 hours. After the disappearance of the 2,6-dichloroaniline was confirmed by gas chromatography (area percentage method), 3 ml of methanol and 3.49 g (30.8 mmol) of a 30% hydrogen peroxide solution were added, and 2.8 g (12.3 mmol) of a 25% aqueous potassium hydroxide solution was added dropwise while the temperature of the reaction liquid was adjusted to 40° C. or less. After the completion of the dropwise addition, the mixture was stirred at room temperature overnight, and the reaction was completed. After the completion of the reaction, 30 ml of toluene and 20 ml of water were added, and the mixture was stirred for a while, and filtered. The filtrate was separated. The obtained organic phase was washed with 10 ml of water, and then heated to reflux, and dehydrated. Thus, a toluene solution of 2,6-dichloronitrobenzene was obtained. This solution was analyzed by gas chromatography by the absolute calibration method, and as a result, the yield was 80%. The amount of the potassium hydroxide added is sufficient to make the pH condition alkaline.

Example 4

Production of 2,6-Dichloronitrobenzene

A solution of 7.5 g (30 mmol) of tungstic acid, 5.2 g (52 mmol) of concentrated sulfuric acid, 32.7 g (200 mmol) of 2,6-dichloroaniline, and 6.9 g (19 mmol) of tetrabutylammonium hydrogen sulfate in 74 ml of a toluene was heated to 47° C., and 53 ml (600 mmol) of a 35% hydrogen peroxide solution was added dropwise over 10 hours. The pH value at this time was 0.3. After the completion of the dropwise addition, the mixture was stirred at 47° C. for 4 hours. After the disappearance of the 2,6-dichloroaniline was confirmed by HPLC analysis (area percentage method), 230 ml of toluene and 20 g (160 mmol) of a 25% aqueous sodium hydroxide solution were added. The pH value at this time was 13.5. The reaction liquid was separated at 75° C., and 91 g of the aqueous layer was removed. Then, the obtained organic layer was cooled to 60° C. or less. 35 g (300 mmol) of a 48% aqueous potassium hydroxide solution was added, and 34 ml (400 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by gas chromatography by the absolute calibration method, and as a result, the yield was 81%.

Example 5

Production of 2,6-Dichloronitrobenzene

A solution of 7.5 g (30 mmol) of tungstic acid, 5.2 g (52 mmol) of concentrated sulfuric acid, 32.7 g (200 mmol) of 2,6-dichloroaniline, and 5.84 g (20 mmol) of myristyltrimethylammonium bromide in 74 ml of a toluene was heated to 47° C., and 53 ml (600 mmol) of a 35% hydrogen peroxide solution was added dropwise over 10 hours. The pH value at this time was 0.3. After the completion of the dropwise addition, the mixture was stirred at 47° C. for 4 hours. After the disappearance of the 2,6-dichloroaniline was confirmed by HPLC analysis (area percentage method), 230 ml of toluene and 20 g (160 mmol) of a 25% aqueous sodium hydroxide solution were added. The pH value at this time was 13.5. The reaction liquid was separated at 75° C., and 91 g of the aqueous layer was removed. Then, the obtained organic layer was cooled to 60° C. or less. 35 g (300 mmol) of a 48% aqueous potassium hydroxide solution was added, and 34 ml (400 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by gas chromatography by the absolute calibration method, and as a result, the yield was 81%.

Example 6

Production of 2,6-Dichloronitrobenzene

A solution of 7.5 g (30 mmol) of tungstic acid, 5.2 g (52 mmol) of concentrated sulfuric acid, 32.7 g (200 mmol) of 2,6-dichloroaniline, and 10.1 g (20 mmol) of trioctylmethylammonium chloride in 74 ml of a toluene was heated to 47° C., and 53 ml (600 mmol) of a 35% hydrogen peroxide solution was added dropwise over 10 hours. The pH value at this time was 0.3. After the completion of the dropwise addition, the mixture was stirred at 47° C. for 4 hours. After the disappearance of the 2,6-dichloroaniline was confirmed by HPLC analysis (area percentage method), 230 ml of toluene and 20 g (160 mmol) of a 25% aqueous sodium hydroxide solution were added. The pH value at this time was 13.5. The reaction liquid was separated at 75° C., and 91 g of the aqueous layer was removed. Then, the obtained organic layer was cooled to 60° C. or less. 35 g (300 mmol) of a 48% aqueous potassium hydroxide solution was added, and 34 ml (400 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by gas chromatography by the absolute calibration method, and as a result, the yield was 90%.

Example 7

Production of 2,6-Dichloronitrobenzene

A solution of 7.5 g (30 mmol) of tungstic acid, 5.2 g (52 mmol) of concentrated sulfuric acid, 32.7 g (200 mmol) of 2,6-dichloroaniline, and 10.1 g (20 mmol) of trioctylmethylammonium chloride in 74 ml of a chlorobenzene was heated to 47° C., and 53 ml (600 mmol) of a 35% hydrogen peroxide solution was added dropwise over 10 hours. The pH value at this time was 0.3. After the completion of the dropwise addition, the mixture was stirred at 47° C. for 4 hours. After the disappearance of the 2,6-dichloroaniline was confirmed by HPLC analysis (area percentage method), 243 g (2.16 mol) of chlorobenzene and 20 g (160 mmol) of a 25% aqueous sodium hydroxide solution were added. The pH value at this time was 13.5. The reaction liquid was separated at 75° C., and 91 g of the aqueous layer was removed. Then, the obtained organic layer was cooled to 60° C. or less. 35 g (300 mmol) of a 48% aqueous potassium hydroxide solution was added, and 34 ml (400 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by gas chromatography by the absolute calibration method, and as a result, the yield was 70%.

Example 8

Production of 2,6-Dichloronitrobenzene

A solution of 7.5 g (30 mmol) of tungstic acid, 5.2 g (52 mmol) of concentrated sulfuric acid, 32.7 g (200 mmol) of 2,6-dichloroaniline, and 5.84 g (20 mmol) of myristyltrimethylammonium bromide in 74 ml of a chlorobenzene was heated to 47° C., and 53 ml (600 mmol) of a 35% hydrogen peroxide solution was added dropwise over 10 hours. The pH value at this time was 0.3. After the completion of the dropwise addition, the mixture was stirred at 47° C. for 4 hours. After the disappearance of the 2,6-dichloroaniline was confirmed by HPLC analysis (area percentage method), 220 ml of chlorobenzene and 20 g (160 mmol) of a 25% aqueous sodium hydroxide solution were added. The pH value at this time was 13.5. The reaction liquid was separated at 75° C., and 91 g of the aqueous layer was removed. Then, the obtained organic layer was cooled to 60° C. or less. 35 g (300 mmol) of a 48% aqueous potassium hydroxide solution was added, and 34 ml (400 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by gas chromatography by the absolute calibration method, and as a result, the yield was 63%.

Example 9

Production of 2,6-Dichloronitrobenzene

A solution of 7.5 g (30 mmol) of tungstic acid, 5.2 g (52 mmol) of concentrated sulfuric acid, 32.7 g (200 mmol) of 2,6-dichloroaniline, and 6.9 g (20 mmol) of tetrabutylammonium hydrogen sulfate in 74 ml of a chlorobenzene was heated to 47° C., and 53 ml (600 mmol) of a 35% hydrogen peroxide solution was added dropwise over 10 hours. The pH value at this time was 0.3. After the completion of the dropwise addition, the mixture was stirred at 47° C. for 4 hours. After the disappearance of the 2,6-dichloroaniline was confirmed by HPLC analysis (area percentage method), 220 ml of chlorobenzene and 20 g (160 mmol) of a 25% aqueous sodium hydroxide solution were added. The pH value at this time was 13.5. The reaction liquid was separated at 75° C., and 91 g of the aqueous layer was removed. Then, the obtained organic layer was cooled to 60° C. or less. 35 g (300 mmol) of a 48% aqueous potassium hydroxide solution was added, and 34 ml (400 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by gas chromatography by the absolute calibration method, and as a result, the yield was 62%.

Example 10

Production of Methyl 3-Chloro-2-nitrobenzoate

A solution of 7.1 g (28.5 mmol) of tungstic acid, 4.9 g (48.5 mmol) of concentrated sulfuric acid, 35.6 g (190 mmol) of methyl 2-amino-3-chlorobenzoate, and 6.9 g (19 mmol) of tetrabutylammonium hydrogen sulfate in 74 ml of toluene was heated to 47° C., and 50 ml (570 mmol) of a 35% hydrogen peroxide solution was added dropwise over 10 hours. The pH value at this time was 0.3. After the completion of the dropwise addition, the mixture was stirred at 47° C. for 4 hours. After the disappearance of the methyl 2-amino-3-chlorobenzoate was confirmed by HPLC analysis (area percentage method), 189.4 g (2.06 mol) of toluene and 19 g (150 mmol) of a 25% aqueous sodium hydroxide solution were added. The pH value at this time was 7.5. The reaction liquid was separated at 75° C., and the aqueous layer was removed.

Then, the obtained organic layer was cooled to 60° C. or less. 5.2 g (61.9 mmol) of sodium hydrogen carbonate and 5.2 ml of water were added, and 25 ml (285 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by HPLC by the absolute calibration method, and as a result, the yield was 72%.

Example 11

Production of Methyl 3-Chloro-2-nitrobenzoate

A solution of 7.1 g (28.5 mmol) of tungstic acid, 4.9 g (48.5 mmol) of concentrated sulfuric acid, 35.6 g (190 mmol) of methyl 2-amino-3-chlorobenzoate, and 5.84 g (20 mmol) of myristyltrimethylammonium bromide in 74 ml of toluene was heated to 47° C., and 50 ml (570 mmol) of a 35% hydrogen peroxide solution was added dropwise over 10 hours. The pH value at this time was 0.3. After the completion of the dropwise addition, the mixture was stirred at 47° C. for 4 hours. After the disappearance of the methyl 2-amino-3-chlorobenzoate was confirmed by HPLC analysis (area percentage method), 189.4 g (2.06 mol) of toluene and 19 g (150 mmol) of a 25% aqueous sodium hydroxide solution were added. The pH value at this time was 7.5. The reaction liquid was separated at 75° C., and 91 g of the aqueous layer was removed. Then, the obtained organic layer was cooled to 60° C. or less. 5.2 g (61.9 mmol) of sodium hydrogen carbonate and 5.2 ml of water were added, and 25 ml (285 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by HPLC by the absolute calibration method, and as a result, the yield was 72%.

Example 12

Production of Methyl 3-Chloro-2-nitrobenzoate

A solution of 7.1 g (28.5 mmol) of tungstic acid, 4.9 g (48.5 mmol) of concentrated sulfuric acid, 35.6 g (190 mmol) of methyl 2-amino-3-chlorobenzoate, and 10.1 g (20 mmol) of trioctylmethylammonium chloride in 74 ml of toluene was heated to 47° C., and 50 ml (570 mmol) of a 35% hydrogen peroxide solution was added dropwise over 10 hours. The pH value at this time was 0.3. After the completion of the dropwise addition, the mixture was stirred at 47° C. for 4 hours. After the disappearance of the methyl 2-amino-3-chlorobenzoate was confirmed by HPLC analysis (area percentage method), 189.4 g (2.06 mol) of toluene and 19 g (150 mmol) of a 25% aqueous sodium hydroxide solution were added. The pH value at this time was 7.5. The reaction liquid was separated at 75° C., and 91 g of the aqueous layer was removed. Then, the obtained organic layer was cooled to 60° C. or less. 5.2 g (61.9 mmol) of sodium hydrogen carbonate and 5.2 ml of water were added, and 25 ml (285 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by HPLC by the absolute calibration method, and as a result, the yield was 74%.

Example 13

Production of Methyl 3-Chloro-2-nitrobenzoate

A solution of 7.1 g (28.5 mmol) of tungstic acid, 4.9 g (48.5 mmol) of concentrated sulfuric acid, 35.6 g (190 mmol) of methyl 2-amino-3-chlorobenzoate, and 6.9 g (19 mmol) of tetrabutylammonium hydrogen sulfate in 74 ml of chlorobenzene was heated to 47° C., and 50 ml (570 mmol) of a 35% hydrogen peroxide solution was added dropwise over 10 hours. The pH value at this time was 0.3. After the completion of the dropwise addition, the mixture was stirred at 47° C. for 4 hours. After the disappearance of the methyl 2-amino-3-chlorobenzoate was confirmed by HPLC analysis (area percentage method), 243 g (2.06 mol) of chlorobenzene and 19 g (150 mmol) of a 25% aqueous sodium hydroxide solution were added. The pH value at this time was 7.5. The reaction liquid was separated at 75° C., and 91 g of the aqueous layer was removed. Then, the obtained organic layer was cooled to 60° C. or less. 5.2 g (61.9 mmol) of sodium hydrogen carbonate and 5.2 ml of water were added, and 25 ml (285 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by HPLC by the absolute calibration method, and as a result, the yield was 72%.

Example 14

Production of Methyl 3-Chloro-2-nitrobenzoate

A solution of 7.1 g (28.5 mmol) of tungstic acid, 4.9 g (48.5 mmol) of concentrated sulfuric acid, 35.6 g (190 mmol) of methyl 2-amino-3-chlorobenzoate, and 5.84 g (20 mmol) of myristyltrimethylammonium bromide in 74 ml of chlorobenzene was heated to 47° C., and 50 ml (570 mmol) of a 35% hydrogen peroxide solution was added dropwise over 10 hours. The pH value at this time was 0.3. After the completion of the dropwise addition, the mixture was stirred at 47° C. for 4 hours. After the disappearance of the methyl 2-amino-3-chlorobenzoate was confirmed by HPLC analysis (area percentage method), 243 g (2.06 mol) of chlorobenzene and 19 g (150 mmol) of a 25% aqueous sodium hydroxide solution were added. The pH value at this time was 7.5. The reaction liquid was separated at 75° C., and 91 g of the aqueous layer was removed. Then, the obtained organic layer was cooled to 60° C. or less. 5.2 g (61.9 mmol) of sodium hydrogen carbonate and 5.2 ml of water were added, and 25 ml (285 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by HPLC by the absolute calibration method, and as a result, the yield was 70%.

Example 15

Production of Methyl 3-Chloro-2-nitrobenzoate

A solution of 7.1 g (28.5 mmol) of tungstic acid, 4.9 g (48.5 mmol) of concentrated sulfuric acid, 35.6 g (190 mmol) of methyl 2-amino-3-chlorobenzoate, and 10.1 g (20 mmol) of trioctylmethylammonium chloride in 74 ml of a chlorobenzene was heated to 47° C., and 50 ml (570 mmol) of a 35% hydrogen peroxide solution was added dropwise over 10 hours. The pH value at this time was 0.3. After the completion of the dropwise addition, the mixture was stirred at 47° C. for 4 hours. After the disappearance of the methyl 2-amino-3-chlorobenzoate was confirmed by HPLC analysis (area percentage method), 243 g (2.06 mol) of chlorobenzene and 19 g (150 mmol) of a 25% aqueous sodium hydroxide solution were added. The pH value at this time was 7.5. The reaction liquid was separated at 75° C., and 91 g of the aqueous layer was removed. Then, the obtained organic layer was cooled to 60° C. or less. 5.2 g (61.9 mmol) of sodium hydrogen carbonate and 5.2 ml of water were added, and 25 ml (285 mmol) of a 35% hydrogen peroxide solution was added dropwise while the reaction temperature was adjusted to 60° C. or less. After the completion of the dropwise addition, the mixture was stirred at 60° C. for 2 hours, and the reaction was completed. The reaction liquid was separated at room temperature. The obtained organic layer was analyzed by HPLC by the absolute calibration method, and as a result, the yield was 76%.

Example 16

Production of 2-Amino-3-chlorobenzoic Acid (Using Ammonia Water)

30 g (157 mmol) of 2,3-dichlorobenzoic acid and 0.78 g (7.85 mmol) of copper(I) chloride were weighed into an autoclave, and 95.6 g (1570 mmol) of 28% ammonia water was added. The autoclave was sealed, and heated in an oil bath at 130° C. and 8 atmospheres for 20 hours. After the completion of the reaction, the autoclave was cooled to room temperature, and the reaction mixture was transferred into a reaction flask, and heated at 90° C. to remove the ammonia. Then, the reaction solution was cooled to room temperature, and the pH value was adjusted to 3 using hydrochloric acid. The precipitated crystals were filtered and dried to obtain 19.1 g of 2-amino-3-chlorobenzoic acid as white crystals with a yield of 71%.

$^1$H-NMR (300 MHz, CDCl$_3$, σ): 6.29 (br, 2H), 6.62 (dd, J=8.0, 8.0 Hz, 1H), 7.47 (d, J=8.0 Hz, 1H), 7.89 (d, J=8.0 Hz, 1H)

Example 17

Production of 2-Amino-3-chlorobenzoic Acid (Using Ammonia Gas)

70 ml of methanol was added to an autoclave, and cooled to −70° C., and 16 g (942 mmol) of a generated ammonia gas was added. 30 g (157 mmol) of 2,3-dichlorobenzoic acid and 0.78 g (7.85 mmol) of copper(I) chloride were added. The autoclave was sealed, and heated in an oil bath at 130° C. and 30 atmospheres for 20 hours. After the completion of the reaction, the autoclave was cooled to room temperature, and the reaction mixture was transferred into a reaction flask. 100 ml of water was added to the reaction solution, and the reaction solution was heated in an oil bath at 100° C. to remove the ammonia and the methanol. Then, the reaction solution was cooled to room temperature, and hydrochloric acid was added to adjust the pH value to 3. The precipitated crystals were filtered and dried to obtain 21.8 g of 2-amino-3-chlorobenzoic acid as white crystals with a yield of 81%.

Example 18

Production of Methyl 2-Amino-3-chlorobenzoate 85.5 g (0.50 mol) of 2-amino-3-chlorobenzoic acid, 300 ml of MIBK (methyl isobutyl ketone), 16.1 g (0.05 mol) of tetrabutylammonium bromide, and 69.4 g (0.55 mol) of dimethyl sulfate were added to a 1000 ml four-necked flask equipped with a stirrer, a reflux condenser, a thermometer, and a dropping funnel, and a mixture of 76.0 g (0.55 mol) of potassium carbonate and 150 ml of MIBK was added dropwise with stirring at 20° C. Then, the mixture was stirred at room temperature for 1 hour. 250 ml of water was added to the reaction mixture, and the reaction solution was separated at room temperature. Then, the MIBK phase was washed with 250 ml of water, and the MIBK was distilled off under reduced pressure. 88.2 g of methyl 2-amino-3-chlorobenzoate as brown crystals was obtained with a yield of 95%.

Melting point: 36° C.

$^1$H-NMR (300 MHz, CDCl$_3$, σ): 7.79 (d, J=8.0 Hz, 1H), 7.384 (d, J=8.0 Hz, 1H), 6.561 (dd, J=8.0, 8.0 Hz, 1H), 6.260 (brs, 2H), 3.866 (s, 3H)

LC-MS (m/z): 186.0 [M+H]+

Example 19

Production of Methyl 2-Amino-3-chlorobenzoate 5.13 g (0.03 mol) of 2-amino-3-chlorobenzoic acid, ml of toluene, 0.97 g (0.003 mol) of tetrabutylammonium bromide, and 4.54 g (0.04 mol) of dimethyl sulfate were added to a 100 ml four-necked flask equipped with a stirrer, a reflux condenser, a thermometer, and a dropping funnel, and a mixture of 4.56 g (0.033 mol) of potassium carbonate and 9 ml of toluene was added dropwise with stirring at 80° C. Then, the mixture was stirred at 80° C. for 1 hour. The solution was analyzed by HPLC by the absolute calibration method, and as a result, the yield was 96%.

Example 20

Production of Methyl 2-Amino-3-chlorobenzoate 5.13 g (0.03 mol) of 2-amino-3-chlorobenzoic acid and 24 ml (0.59 mol) of methanol were added to a 100 ml four-necked flask equipped with a stirrer, a reflux condenser, a thermometer, and a dropping funnel, and a hydrogen chloride gas was blown in with stirring at 65° C. After 10 hours, the reaction solution was analyzed by HPLC by the absolute calibration method, and as a result, the yield was 75%.

Example 21

Production of Methyl 2-Amino-3-chlorobenzoate 3 ml (0.074 mol) of methanol was added to a 50 ml four-necked flask equipped with a stirrer, a reflux condenser, a thermometer, and a dropping funnel, and 1.43 g (0.012 mol) of thionyl chloride was added dropwise with stirring at −5° C. Then, a mixture of 1.71 g (0.010 mol) of 2-amino-3-chlorobenzoic acid in 2.0 ml (0.049 mol) of methanol was added dropwise with stirring at −5° C. Then, the mixture was stirred at room temperature for 15 hours and at 65° C. for 17 hours. The reaction solution was analyzed by HPLC by the absolute calibration method, and as a result, the yield was 61%.

Comparative Example 1

Method Described in Example 1, Japanese Patent No. 4284999 (Patent Literature 7)

Production of Methyl 3-Chloro-2-nitrobenzoate

A suspension of 0.01 g (0.054 mmol) of tungsten metal in 0.12 g (1.08 mmol) of a 30% hydrogen peroxide solution was heated to 40° C., and stirred for 30 minutes, and then, a solution of 0.2 g (1.08 mmol) of methyl 2-amino-3-chlorobenzoate in 3 g of t-butyl alcohol, and 0.49 g (4.32 mmol) of a 30% hydrogen peroxide solution were added. The pH value at this time was 2.4. Then, the mixture was stirred at 70° C. for 22 hours. This solution was analyzed by HPLC by the absolute calibration method, and as a result, methyl 3-chloro-2-nitrobenzoate, the target material, was 26.6%.

Comparative Example 2

Method Described in Example 5, Japanese Patent No. 4284999 (Patent Literature 7)

Production of Methyl 3-Chloro-2-nitrobenzoate

A suspension of 0.013 g (0.066 mmol) of tungsten carbide in 0.12 g (1.08 mmol) of a 30% hydrogen peroxide solution was stirred at 40° C. for 30 minutes, and then, a solution of 0.2 g (1.08 mmol) of methyl 2-amino-3-chlorobenzoate in 3 g of t-butyl alcohol, and 0.49 g (4.32 mmol) of a 30% hydrogen peroxide solution were added. The pH value at this time was 4.6. Then, the mixture was stirred at 70° C. for 22 hours. This solution was analyzed by HPLC by the absolute calibration method, and as a result, methyl 3-chloro-2-nitrobenzoate, the target material, was 9.0%.

As shown by Comparative Example 1 and Comparative Example 2, it can be said that the conditions in Patent Literature 7 are not effective production methods in the oxidation of 2,6-disubstituted aniline.

(HPLC Analysis Method)

Regarding the details of the above-described HPLC analysis method, the following literatures can be referred to, as required.

(a): The Chemical Society of Japan ed., "Shin Jikken kagaku Koza (New Experimental Chemistry Course) 9 Bunsekikagaku (Analytical Chemistry) II," pp. 86 to 112 (1977), published by Shingo Iizumi, Maruzen Company, Limited (For example, regarding packing material-mobile phase combinations that can be used in the column, pp. 93 to 96 can be referred to.)

(b) The Chemical Society of Japan ed., "Jikken kagaku Koza (Experimental Chemistry Course) 20-1 Bunsekikagaku (Analytical Chemistry)," 5th ed., pp. 130 to 151 (2007), published by Seishiro Murata, Maruzen Company, Limited (For example, regarding the specific usage and conditions of reversed phase chromatography analysis, pp. 135 to 137 can be referred to.)

(Gas Chromatography Analysis Method)

Regarding the details of the above-described gas chromatography analysis method, the following literatures can be referred to, as required.

(c): The Chemical Society of Japan ed., "Shin Jikken kagaku Koza (New Experimental Chemistry Course) 9 Bunsekikagaku (Analytical Chemistry) II," pp. 60 to 86 (1977), published by Shingo Iizumi, Maruzen Company, Limited (d) The Chemical Society of Japan ed., "Jikken kagaku Koza (Experimental Chemistry Course) 20-1 Bunsekikagaku (Analytical Chemistry)," 5th ed., pp. 121 to 129 (2007), published by Seishiro Murata, Maruzen Company, Limited (Method for Measuring pH Value)

The pH value was measured by a glass electrode type hydrogen ion concentration indicator. As the glass electrode type hydrogen ion concentration indicator, specifically, for example, model: HM-20P manufactured by DKK-TOA CORPORATION can be used.

INDUSTRIAL APPLICABILITY

According to the present invention, a novel industrial production method for a nitrobenzene compound, particularly a 2,6-disubstituted nitrobenzene compound, is provided. According to the method of the present invention, the aniline compound represented by general formula (1) can be used as the raw material, and the nitrobenzene compound represented by general formula (2) can be produced with high purity on an industrial scale using hydrogen peroxide, which is inexpensive and becomes harmless water after a reaction, and attracts attention as a clean and excellent oxidant.

In addition, it is not necessary to use high concentration hydrogen peroxide, which requires much caution in work, and the nitrobenzene compound represented by general formula (2) can be produced with good yield on an industrial scale using commercial available about 30% hydrogen peroxide solution.

Further, the nitrobenzene compound represented by general formula (2) can be produced with good yield on an industrial scale even without using a high risk organic peroxy acid such as peracetic acid or trifluoroperacetic acid.

The obtained nitrobenzene compound represented by general formula (2) is a compound useful as an intermediate for the synthesis of various organic compounds, and therefore, the method of the present invention has a high industrial utility value.

The invention claimed is:

1. A method for producing a nitrobenzene compound represented by general formula (2):

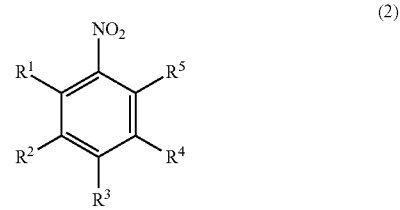

(2)

wherein $R^1$ and $R^5$ are the same or different, and each is a halogen atom, a C1 to C4 alkoxycarbonyl group, a C1 to C4 alkyl group, a C1 to C4 alkoxy group, or a C1 to C4 alkoxy C1 to C4 alkyl group, and $R^2$, $R^3$, and $R^4$ are the same or different, and each is a hydrogen atom, a halogen atom, a C1 to C4 alkyl group, a C1 to C4 alkoxy group, or a C1 to C4 haloalkyl group, the method comprising the steps of:

oxidizing an aniline compound represented by general formula (1):

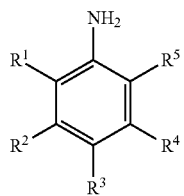

with hydrogen peroxide in the presence of a tungsten compound under an acidic condition, wherein $R^1$, $R^2$, $R^3$, $R^4$, and $R^5$ are the same as described above, and followed by a second oxidizing with hydrogen peroxide by changing the acidic condition to a neutral to alkaline condition to produce a 2,6-disubstituted nitrobenzene compound represented by general formula (2).

2. The method for producing a nitrobenzene compound according to claim 1, wherein the oxidizing of the aniline compound to the nitrobenzene compound is conducted in the presence of a solvent.

3. The method for producing a nitrobenzene compound according to claim 2, wherein the solvent is water, an alcohol, a nitrile, an aromatic hydrocarbon, or a mixed solvent thereof.

4. The method for producing a nitrobenzene compound according to claim 2, wherein the solvent is water.

5. The method for producing a nitrobenzene compound according to claim 2, wherein the solvent is a mixed solvent of water and an aromatic hydrocarbon, and the oxidizing of the aniline compound to the nitrobenzene compound is conducted in the presence of a phase transfer catalyst.

6. The method for producing a nitrobenzene compound according to claim 5, wherein the aromatic hydrocarbon is one or more selected from benzene, chlorobenzene, dichlorobenzene, trichlorobenzene, toluene, xylene, mesitylene, or ethylbenzene.

7. The method for producing a nitrobenzene compound according to claim 1, wherein either one of $R^1$ or $R^5$ in general formula (1) is a C1 to C4 alkoxycarbonyl group and said aniline compound is produced by esterification of an aminobenzoic acid compound represented by general formula (4):

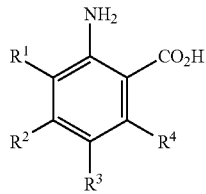

wherein $R^1$, $R^2$, $R^3$, and $R^4$ are the same as described above, and which is obtained by amination of a halogenobenzoic acid compound represented by general formula (3):

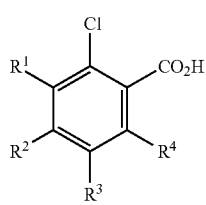

wherein $R^1$, $R^2$, $R^3$, and $R^4$ are the same as described above.

8. The method for producing a nitrobenzene compound according to claim 1, wherein the tungsten compound is tungstic acid.

9. The method for producing a nitrobenzene compound according to claim 1, wherein the tungsten compound is a tungstic acid salt.

10. The method for producing a nitrobenzene compound according to claim 1, wherein the tungsten compound is metal tungsten.

11. The method for producing a nitrobenzene compound according to claim 5, wherein the phase transfer catalyst is a quaternary ammonium salt.

12. The method for producing a nitrobenzene compound according to claim 11, wherein the phase transfer catalyst is one or more selected from tetrabutylammonium bromide, tetrabutylammonium hydrogen sulfate, trioctylmethylammonium chloride, or myristyltrimethylammonium bromide.

13. The method for producing a nitrobenzene compound according to claim 1, wherein a pH condition under the acidic condition is 2.0 or less.

14. The method for producing a nitrobenzene compound according to claim 1, wherein a pH condition under the neutral to alkaline condition is 6.5 to 16.0.

15. The method for producing a nitrobenzene compound according to claim 1, wherein a pH condition under the neutral to alkaline condition is 6.5 to 15.0.

16. The method for producing a nitrobenzene compound according to claim 1, wherein $R^2$, $R^3$, and $R^4$ in general formula (1) are each a hydrogen atom.

17. The method for producing a nitrobenzene compound according to claim 1, wherein $R^1$ and $R^5$ in general formula (1) are the same or different, and each is a halogen atom or a C1 to C4 alkoxycarbonyl group.

18. The method for producing a nitrobenzene compound according to claim 1, wherein $R^1$ and $R^5$ in general formula (1) are each a halogen atom.

19. The method for producing a nitrobenzene compound according to claim 1, wherein $R^1$ in general formula (1) is a halogen atom, and $R^5$ is a C1 to C4 alkoxycarbonyl group.

20. The method for producing a nitrobenzene compound according to claim 1, wherein $R^1$ and $R^5$ in general formula (1) are each a halogen atom, $R^2$, $R^3$, and $R^4$ are each a hydrogen atom, the tungsten compound is a tungstic acid salt, a pH condition under the acidic condition is 2.0 or less, a pH condition under the neutral to alkaline condition is 6.5 to 15.0, the solvent is a mixed solvent of water and one or more kind selected from benzene, chlorobenzene, dichlorobenzene, trichlorobenzene, toluene, xylene, mesitylene, or ethylbenzene, the oxidizing is conducted in the presence of a phase transfer catalyst, and the phase transfer catalyst is one or more selected from tetrabutylammonium bromide, tetrabutylammonium hydrogen sulfate, trioctylmethylammonium chloride, or myristyltrimethylammonium bromide.

21. The method for producing a nitrobenzene compound according to claim 2, wherein $R^1$ in general formula (1) is a halogen atom, $R^5$ is a C1 to C4 alkoxycarbonyl group, $R^2$, $R^3$, and $R^4$ are each a hydrogen atom, the tungsten compound is a tungstic acid salt, a pH condition under the acidic condition is 2.0 or less, a pH condition under the neutral to alkaline condition is 6.5 to 15.0, the solvent is a mixed solvent of water and one or more selected from benzene, chlorobenzene, dichlorobenzene, trichlorobenzene, toluene, xylene, mesitylene, or ethylbenzene, the oxidizing is conducted in the presence of a phase transfer catalyst, and the phase transfer catalyst is one or more selected from tetrabutylammonium bromide, tetrabutylammonium hydrogen sulfate, trioctylmethylammonium chloride, or myristyltrimethylammonium bromide.

* * * * *